United States Patent
Bartol, Jr. et al.

(10) Patent No.: US 7,255,682 B1
(45) Date of Patent: Aug. 14, 2007

(54) SPOT LOCATOR DEVICE

(76) Inventors: Robert J. Bartol, Jr., P.O. Box 190881, Boise, ID (US) 83719; Ema Bartol, P.O. Box 190881, Boise, ID (US) 83719

( * ) Notice: Subject to any disclaimer, the term of this patent is extended or adjusted under 35 U.S.C. 154(b) by 246 days.

(21) Appl. No.: 10/936,981

(22) Filed: Sep. 9, 2004

(51) Int. Cl.
*A61M 5/00* (2006.01)

(52) U.S. Cl. .................................... 604/116

(58) Field of Classification Search ............... 604/116, 604/117, 288.01–288.04; 128/898, 897
See application file for complete search history.

(56) References Cited

U.S. PATENT DOCUMENTS

| | | | |
|---|---|---|---|
| 4,286,584 A * | 9/1981 | Sampson et al. | 128/899 |
| 4,784,646 A * | 11/1988 | Feingold | 604/175 |
| 5,758,667 A * | 6/1998 | Slettenmark | 128/899 |
| 6,173,715 B1 * | 1/2001 | Sinanan et al. | 128/899 |
| 6,588,432 B1 * | 7/2003 | Rehder et al. | 128/899 |

* cited by examiner

*Primary Examiner*—Kevin C. Sirmons
*Assistant Examiner*—Elizabeth MacNeill
(74) *Attorney, Agent, or Firm*—Frank J. McGue

(57) ABSTRACT

A locator device precisely identifies a predetermined spot which is hidden by a skin. The device is an outer washer and an inner washer with both washers being magnetized. The inner washer is positioned underneath the skin to mark the location of the predetermined spot therein. The outer washer aligns with the inner washer when proximate thereto to thereby locate said predetermined spot.

2 Claims, 4 Drawing Sheets

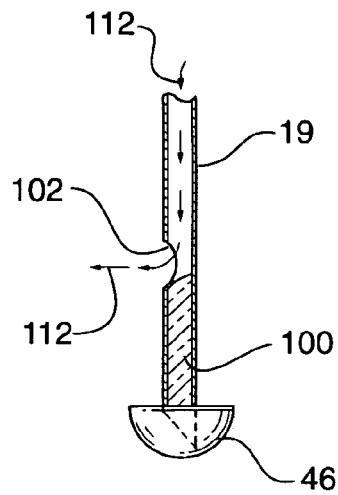
FIG. 10.
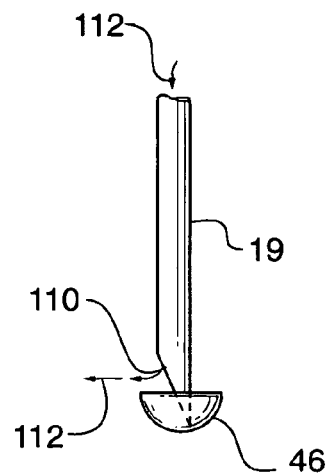
FIG. 11.
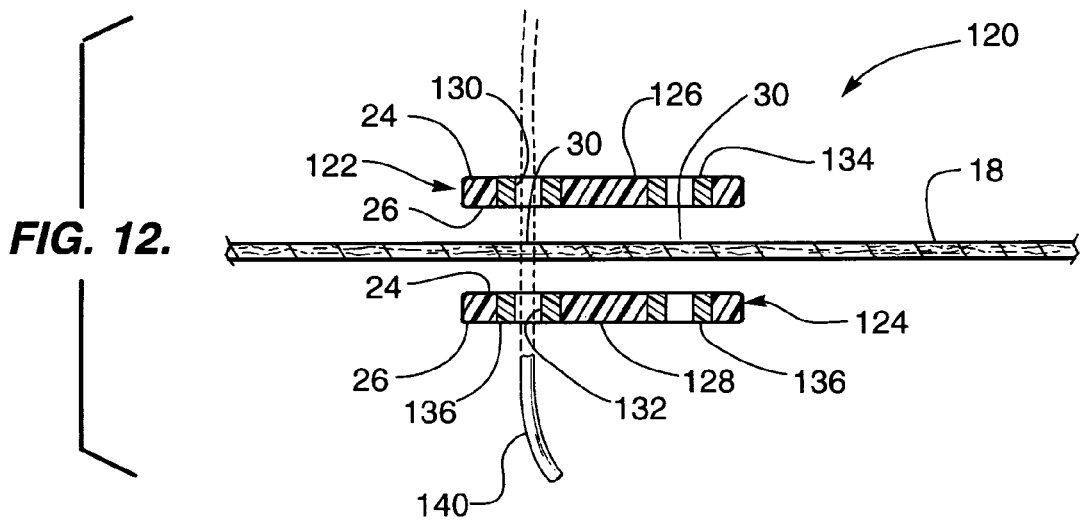
FIG. 12.
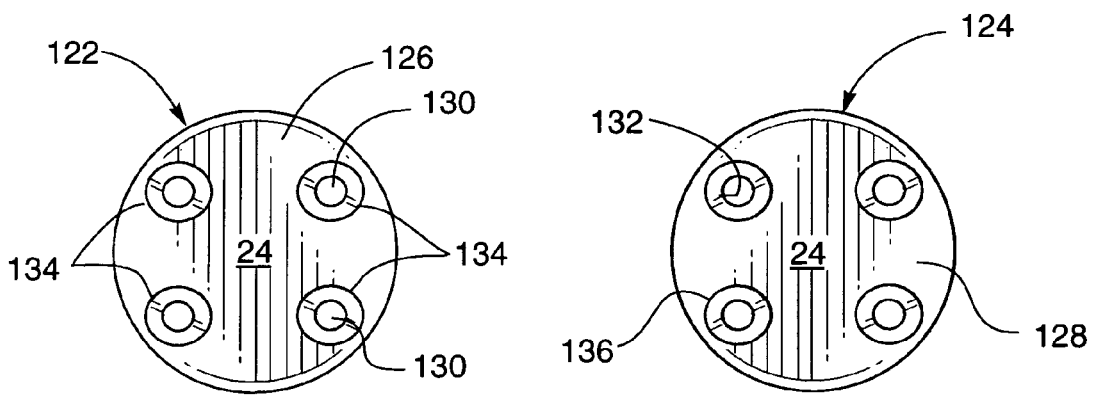
FIG. 13.     FIG. 14.

SPOT LOCATOR DEVICE

TECHNICAL FIELD

This invention relates generally to the field of spot locator devices, and, more particularly, to a device for locating a specific spot or spots through the skin.

BACKGROUND OF THE INVENTION

Often time, it is desired to locate a specific spot under the human skin which is covered by said skin. For example, often in the medical profession drug releasing devices are placed underneath a patient's skin. These devices release medicine at a predetermined rate thereby maintaining a constant level of medicine in the patient's body without the need for frequent injections or infusions of food. However, periodically the medicines within the drug releasing devices must be replenished which requires the use of a syringe puncturing the skin and injecting the medicine into the drug releasing device. However, because the device is buried beneath the skin, often the wielder of the syringe has a difficult time locating the precise spot to puncture.

Thus, there is a need for a device to precisely locate a spot hidden beneath a surface.

Inamed Corporation has developed a tissue expanding system for cosmetic surgery in which employs a high gauss level magnet that is mounted on a gimbal outside a patient's skin. The device is used to detect another high gauss magnet located at the bottom of a dispensing chamber implanted under the skin. The implanted magnet may cause a disruption in the operation of nearby electronic or electrically operated medical devices. In addition, due to its size and complexity, this gimbal mounted magnet is expensive. Further, this device must be sterilized prior to each use.

To use, the gimbal mounted magnet is moved in about above the skin approximately where the implanted magnet is located. This scanning is a necessary part of the process since all implanted devices shift position underneath the skin. Thus, the exact location must be determined before each injection.

When the implanted magnet is detected, a mark is made with a medical marking pen on the skin. The procedure is repeated several times thereby resulting in a plurality of marks on the skin in a group. A syringe is injected into the center of the grouped markings through the skin and into the dispensing chamber. Resistance to the syringe's movement is detected when contact is made with the implanted magnet at the bottom of the dispensing chamber. The contact may, in some instances, cause damage to the needle.

The Inamed Corporation's method and apparatus provides an approximate insertion point but does have a margin of error and is time consuming.

Thus, none of the known prior art disclose the combination set forth herein.

SUMMARY OF THE INVENTION

It is an object of this invention to provide a device for precisely locating a spot hidden beneath a skin surface.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

The present invention may be more readily described by reference to the accompanying drawings in which:

FIG. 10 is side view of one embodiment of a needle useful in the present invention;

FIG. 11 is a side view of another embodiment of a needle useful in the present invention;

FIG. 12 is a cross sectional side view of an alternate multiport locator embodiment of the present invention;

FIG. 13 is a top view of a magnetic disc comprising the outer component of the embodiment of FIG. 12; and FIG. 14 is a top view of another magnetic disc comprising the inner component of the embodiment of FIG. 12.

DESCRIPTION OF THE PREFERRED EMBODIMENT

Figure 1:
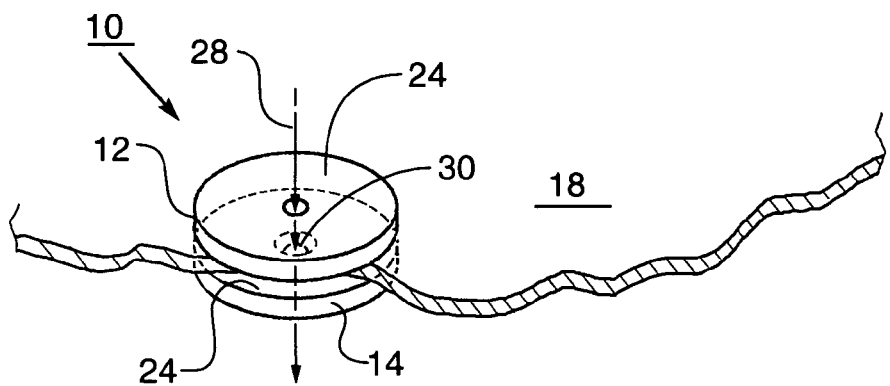
FIG. 1 is a perspective partial cut away view of one embodiment of the present invention.
Figure 2:
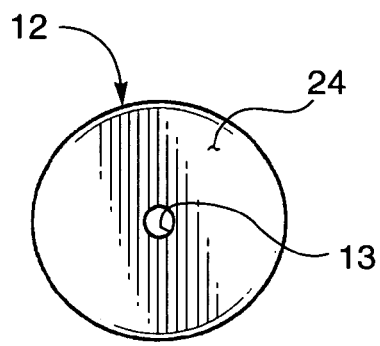
FIGS. 2 and 2A are top and side views of a magnetic disc comprising the outer component of the present invention.
Figure 3:
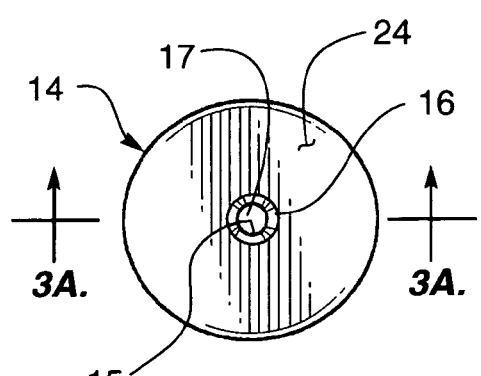
FIGS. 3 and 3A are top and side views of another magnetic disc comprising the inner component of the present invention.
Figure 2A:
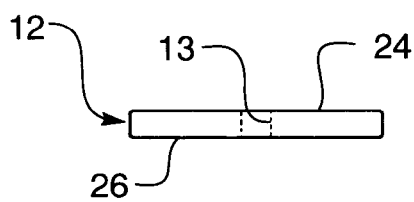
Figure 3A:
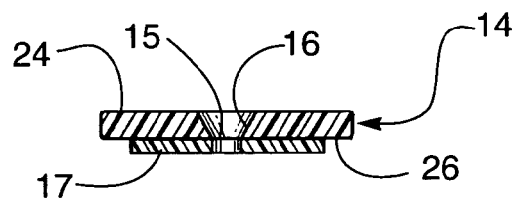

Referring more particularly to the drawings by characters of reference, FIGS. 1-4 disclose combinations of features which constitute the components of a locator device 10 of the present invention. In the illustrated embodiment, locator device 10 comprises an outer washer 12 and an equal sized inner washer 14. Washers 12 and 14 are magnetic as described further below.

To practice the invention, the user first determines a precise spot 30 to be located under a patient's skin 18. Skin 18 is opened and inner washer 14 is positioned on spot 30 with its center marking the location of same. Skin 18 is then re-positioned over inner washer 14 with an axis 28 of said washer 14 oriented perpendicular to skin 18. Skin 18 will heal naturally over inner washer 14.

For exemplary purposes, spot 30 is the location of a drug dispensing device. Note that these are for exemplary purposes and that the invention is not limited to such uses. Those skilled in the art will recognize that the invention is useful in locating a precise spot through the skin surface and has many other uses than those described herein. For example, the invention's use in connection with a tissue expander is discussed below. Another use is to precisely locate feeding tubes for those patient's needing same. In the prior art, feeding tubes often cause infection around the site where said tubes enter the skin. The present invention allows the placement of such feeding tubes underneath the skin thereby lessening this chance of infection.

Each washer 14 and 12 is magnetized whereby one flat surface is a north magnetic pole 24 while the other flat surface is a south magnetic pole 26. Washers 12 and 14 are positioned whereby those surfaces of said washers abutting skin 18 are of opposing poles. In the illustrated example, the surface of inner washer 14 abutting skin 18 is north pole 24 and the surface of outer washer 12 abutting skin 18 is south pole 26. Those skilled in the art will recognize that having the surface of inner washer 14 abutting skin 18 as south pole 26 and the surface of outer washer 12 abutting skin 18 north pole 24 will not change the functionality of said devices. The key is that the surfaces of washers 12 and 14 abutting skin 18 must be opposing poles.

Additionally, the invention is best operated when inner washer 14 is positioned abutting skin 18 and not buried deep within the body. By doing so, the magnetic forces needed to operate device 10 are minimized. The minimization greatly reduces the possibility of disrupting nearby devices which may be implanted in the body or positioned nearby.

Center holes 13 and 15 extend through the centers of outer washer 12 and inner washer 14, respectively. In the preferred embodiment best seen in FIGS. 2, 2a, 3 and 3a, center hole 15 of inner washer 14 is a larger diameter than center hole 13 of outer washer 12 and includes a tapered sidewall 16.

Figure 8:
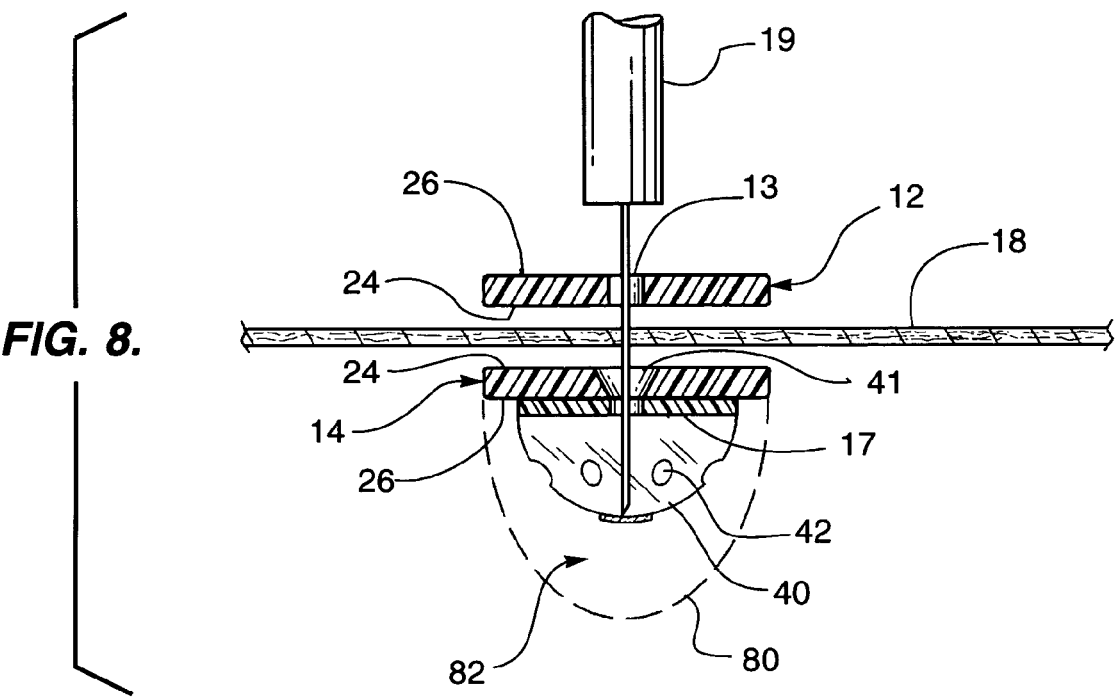
FIG. 8 is a cross sectional side view of an alternate embodiment of the present invention used with a tissue expander.

In the preferred embodiments of FIGS. 1-4, a layer 17 of a self sealing material is mounted on the surface of inner washer 14 which is opposite skin 18. If preferred, said self-sealing material extends into center hole 15 as shown in FIG. 8.

Figure 4:
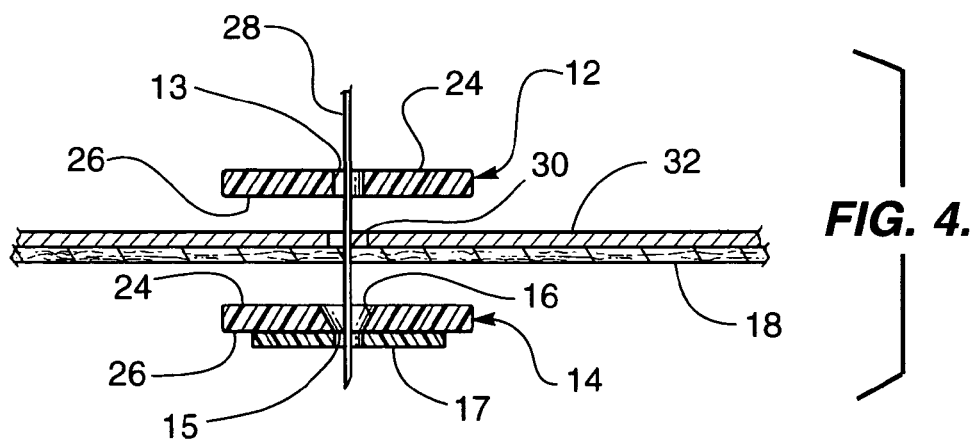
FIG. 4 is a cross sectional side view of the embodiment of FIG. 1 in use with a sheet.

To position the outer washer 12 in one method best seen in FIG. 4, a sheet 32 of a slick material such as Teflon® is placed over skin 18. Sheet 32 includes a hole 33 which is preferably larger than either holes 13 and 15. Outer washer 12 is brought proximate to sheet 32 with, in this example, south pole 26 abutting sheet 32. The magnetic attractive forces from the north pole 24 of inner washer 14 and south pole 26 of outer washer 12 forces washers 12 and 14 into alignment along axis 28 which thereby aligns center holes 13 and 15. Sheet 32 allows easier sliding movement of washers 12 and 14 into alignment. Once washers 12 and 14 are aligned, sheet 32 can be slid about skin 18 to align hole 33 thereof with holes 13 and 15. Those skilled in the art will recognize other methods of accomplishing same are possible, including, but not limited to, use of lubricating agents such as lotions, jellies or oils applied to skin 18.

Figure 5:
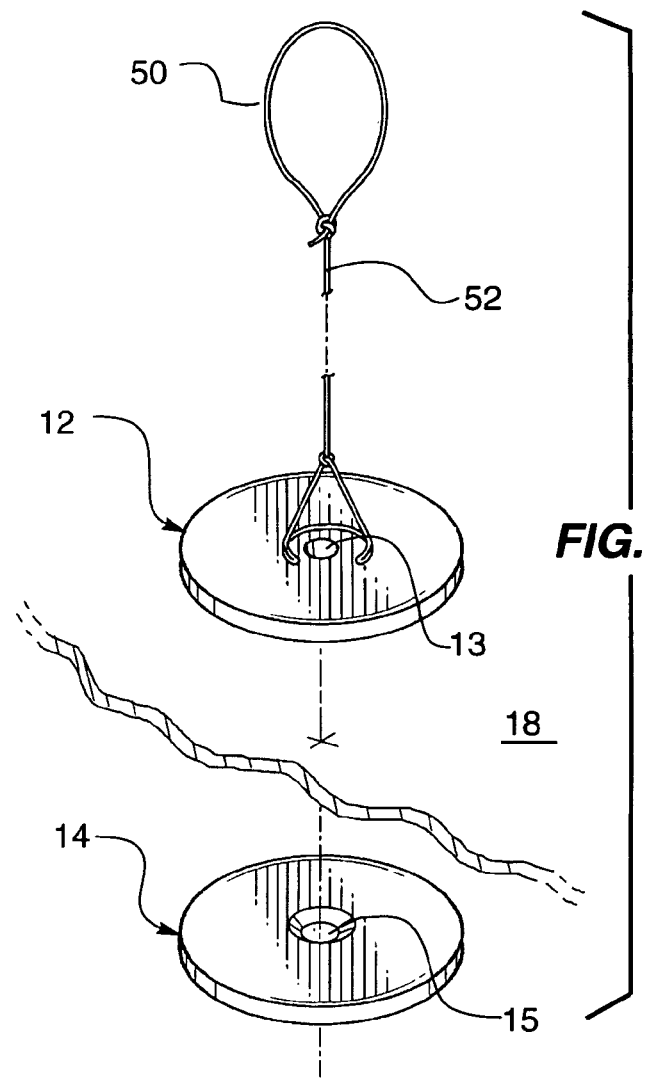
FIG. 5 is a perspective view of an alternate embodiment of the present invention.

In another variation seen in FIG. 5, a finger loop 50 is mounted at one end of a string member 52. The other end of string member 52 is affixed to outer washer 12. In use, the user suspends washer 12 over the proximate location of inner washer 14 using finger loop 50. Once the outer washer 12 is magnetically attracted to inner washer 14, finger loop 50 and string member 52 are used to slowly lower outer washer 12 into contact with skin 18. Since friction is virtually non-existent, magnetic forces align holes 13 and 15 without the need to slide outer washer 12 over skin 18 thereby obviating the need for a sheet 32 or lubricating agents.

Figure 6:
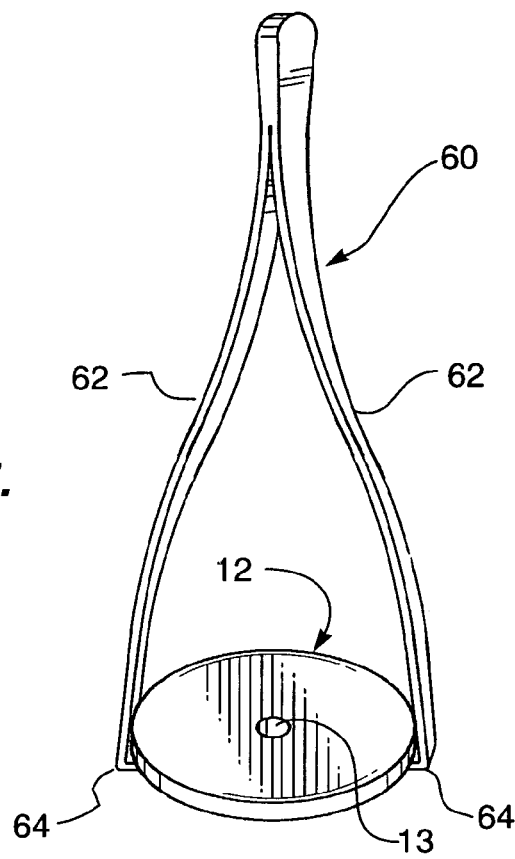
FIG. 6 is a perspective view of an alternate method of aligning the present invention.

In another variation seen in FIG. 6, a tweezer device 60 having two juxtaposed arms 62 with inwardly extending grips 64 is employed to grasp outer washer 12. As in the prior discussion regarding the embodiment of FIG. 5, the user suspends washer 12 over the proximate location of inner washer 14 using tweezer device 60. Once the outer washer 12 is magnetically attracted to inner washer 14, tweezer device 60 is used to slowly lower outer washer 12 into contact with skin 18. Since friction is virtually non-existent, magnetic forces align holes 13 and 15 without the need to slide outer washer 12 over skin 18 thereby again obviating the need for a sheet 32 or lubricating agents.

The alignment of holes 13 and 15 marks precisely spot 30 for the user outside skin 18. Once aligned, needles or syringes 19 are employed by inserting same through holes 13 and 15.

The key to the present invention is the use of magnetic fields to align an inner magnet with an outer magnet. This alignment is accomplished without the need to refer to x-y coordinates and the like for placement. The present examples using washers 12 and 14 are illustrative and are not meant to limit the invention to the use of discs only.

Those skilled in the art will recognize one advantage to the use of washers 12 and 14 is that such devices are very inexpensive and easy to manufacture. Because of the inexpensive nature of said washers 12 and 24, outer washer can simply be disposed of after each use thereby avoiding the need for expensive, time consuming re-sterilization.

Figure 7:
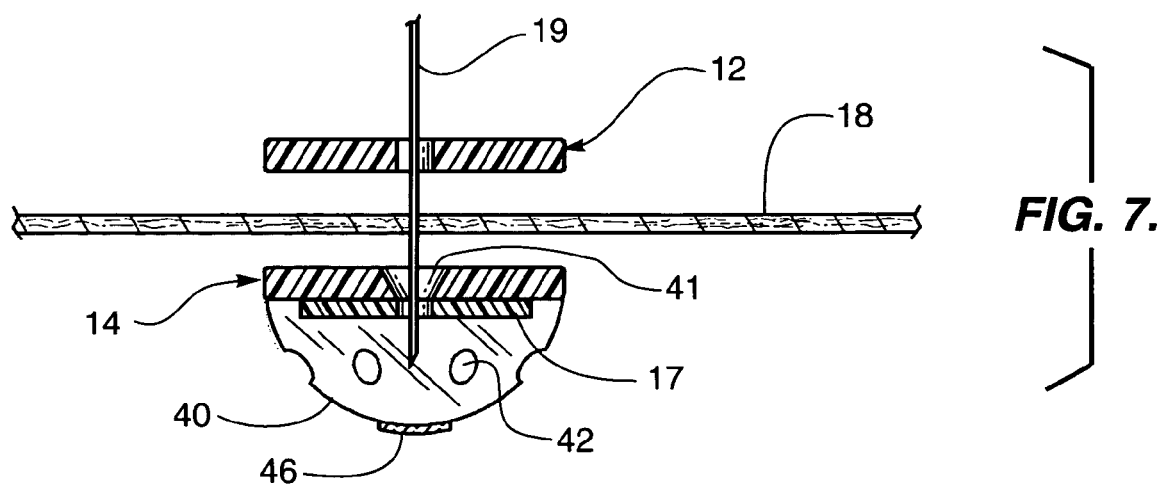
FIG. 7 is a cross sectional side view of an alternate embodiment of the present invention used with a shell.

In the alternate embodiment of FIG. 7, a dispensing chamber 40 having one or more exit holes 42 is mounted to the surface of inner washer 14 opposite skin 18. Exit holes 42 allow the contents of dispensing chamber 40 to seep into the surrounding matter at a controlled rate, as, for example, to dispense medicine to a patient.

To refill dispensing chamber 40 as needed, outer washer 12 is used as in one of the methods previously described. Syringe needle 19 is then inserted from the outside of skin 18 through center holes 13 and 15 and self sealing material 17 and hence into dispensing chamber 40. In this variation, self-sealing material 17 includes an extension 41 into center hole 15. A thickened silicone or a ceramic coating 46 is provided to that portion of dispensing chamber 40 which is aligned with and positioned opposite center holes 13 and 15. Coating 46 prevents needle 19 from puncturing dispensing chamber 40. In addition, the added resistance felt when syringe 19 encounters coating 46 tells the user when needle 19 is properly positioned. Once needle 19 is positioned, medicine can be injected to fill or refill dispensing chamber 40.

In the alternate embodiment of FIG. 8, the present invention is used in connection with a tissue expander 82. As described previously in connection with FIG. 7, dispensing chamber 40 having exit holes 42 is mounted to the surface of inner washer 14 opposite skin 18. However, instead of allowing the contents of dispensing chamber 40 to seep into surrounding tissue, in this embodiment, exit holes 42 allow the contents of dispensing chamber 40 to seep into a bladder 80 at a controlled rate thereby expanding bladder 80, and the surrounding tissue, as desired.

To refill dispensing chamber 40 as needed, outer washer 12 is used as in one of the methods previously described. Syringe needle 19 is then inserted from the outside of skin 18 through center holes 13 and 15 and self sealing material 17 and hence into dispensing chamber 40. In this variation, self-sealing material 17 includes an extension 41 into center hole 15. A thickened silicone or a ceramic coating 46 is provided to dispensing chamber 40 which is aligned with center holes 13 and 15 from needle 19 from puncturing dispensing chamber 40. In addition, the added resistance felt when syringe 19 encounters coating 46 tells the user when needle 19 is properly positioned. Once needle 19 is positioned, a solution can be injected to fill or refill dispensing chamber 40, and hence bladder 80, until a predetermined amount has been injected.

Figure 9:
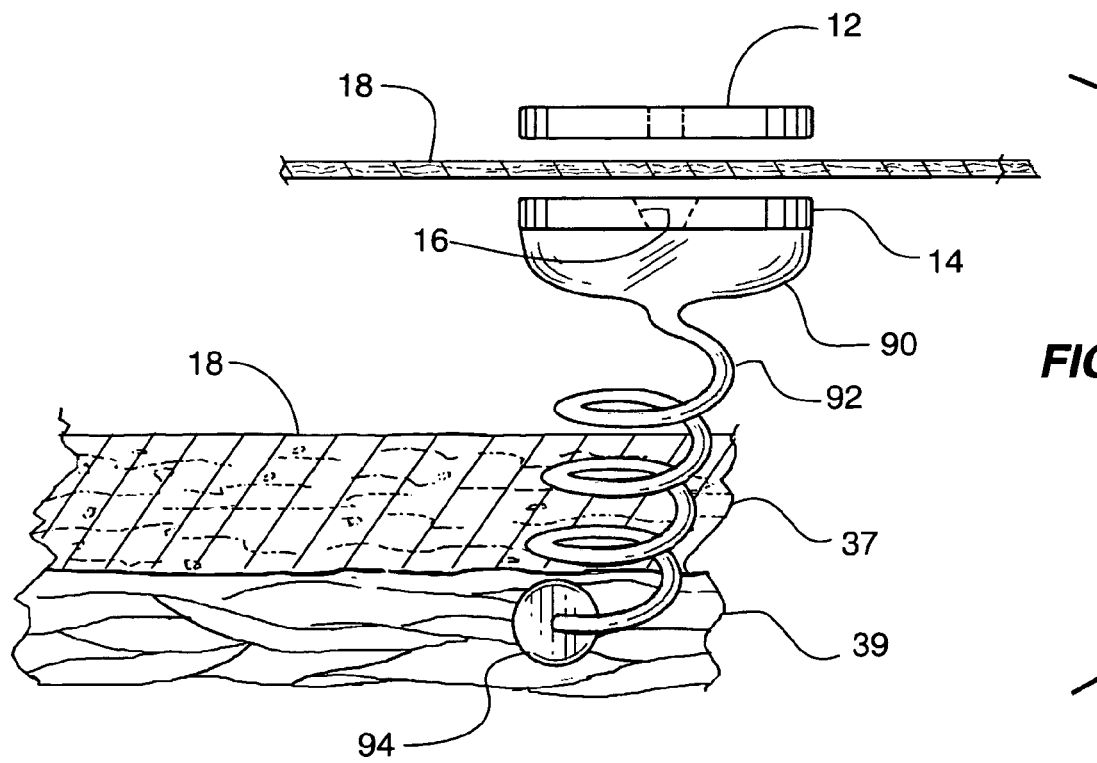
FIG. 9 is a partial cross sectional side view of an alternate embodiment of the present invention.

Still another variation seen in FIG. 9 provides a dispensing chamber 90 positioned as described previously for FIG. 7 but having a coil 92 extending therefrom deeper into the tissues 37 and 39 underneath skin 18. At the end of coil 92, a release mechanism 94 allows medicine to seep into the deeper tissues as desired. This variant allows for dispensing of medicine into deeper tissues while still allowing use of surface magnets with the advantages previously discussed.

In addition, use of the variation of FIG. 9 eliminates or significantly reduces the dangers of nerve damage which can be caused by injection needles as needle or syringe 19 is always injected into a known protected area. Use of coil 92 permits medicines to reach deep within the tissues even though a relatively short needle or syringe 19 is employed. Further, in somewhat of a reverse use, needle or syringe 19 can be used in conjunction with coil 92 and chamber 90 to remove or drain areas deep within the body, for example, after surgery.

While the usual needle 19 configuration is operable with the present invention, two variations of needle 19 construction are shown in FIGS. 10 and 11. In FIG. 11, the distal end of needle 19 includes a larger opening 110 to facilitate movement of liquid 112 therethrough. In FIG. 10, the distal end 100 of needle 19 is solid with an opening 102 positioned above said solid distal end whereby liquid 112 flows from needle 19 without potential obstruction from coating 46.

For those patients who require multiple injection points, a multiport locator device 120 is shown in FIGS. 12-14. Multiport locator device 120 includes an outer disc 122 and an inner disc 124. Each disc 122, 124 comprises a body portion 126, 128, respectively, made of a non-ferrous (non-magnetic) material. Each body portion 126, 128 includes a plurality of paired and matching openings 130, 132. When discs 122, 124 are placed in abutting position, the paired and matching openings 130, 132 are aligned. In the illustrated embodiment of FIGS. 12-14, four openings 130, 132 are circular though other shapes are certainly possible as those skilled in the art will recognize.

A pair of ferrous (magnetic) washers 134, 136 are mounted to each corresponding opening 130, 132, respectively are magnetized whereby one flat surface is a north magnetic pole 24 while the other flat surface is a south magnetic pole 26. Each of the paired and matching washers 134 and 136 are positioned whereby those surfaces of said washers abutting skin 18 are of opposing poles. The key to the invention is that the surfaces of paired and matching ferrous washers 134, 136 abutting skin 18 must be opposing poles. Center holes 135 and 137 extend through the centers of each ferrous washer 134, 136, respectively.

To practice the invention, the user first determines the precise location of the corresponding plurality of spots 30 to be located under a patient's skin 18. Skin 18 is opened and inner disc 124 is positioned whereby each of the plurality of spots 30 is matched with one of the corresponding plurality of paired center holes 135, 137. Skin 18 is then re-positioned over inner disc 124 with an axis of said ferrous washer 136 oriented perpendicular to skin 18. Skin 18 will heal naturally over inner disc 124.

The outer disc 126 is aligned with inner disc 124 using methods previously described. Needles 19 are inserted through holes 135, 137 and into, for example tube 140, or directly into the skin, or into mechanisms such as those described previously. Each of the plurality of paired holes 135, 137 can lead to a common dispensing chamber, or to differing chambers as desired and predetermined by the medical facts relating to a particular patient.

Those skilled in the art will recognize that the present invention is not meant to be limited to the specific shapes and structures described. Other shapes and structures can be employed without departing from the scope of the intended invention. In addition, the present invention is useful in accomplishing other medically related tasks. For example, other uses could include providing a battery check on an implanted battery powered medical device or locating an identification chip now implanted in family pets are certainly contemplated within the scope of the present invention.

Although only certain embodiments have been illustrated and described, it will be apparent to those skilled in the art that various changes and modifications may be made therein without departing from the spirit of the invention or from the scope of the appended claims.

What is claimed is:

1. A multiport locator device for patients who require multiple injection points, the multiport locator device comprising:

an outer body portion and an inner body portion made of a non-ferrous material, the inner body portion including a plurality of openings which are paired and matched with a corresponding plurality of openings in the outer body portion whereby when the body portions are placed in abutting position, each of the plurality of openings in one of said body portions is aligned with a corresponding opening in the other of the body portions, a pair of ferrous washers being mounted to each of the plurality of paired and matching openings, the pair of ferrous washers being magnetized whereby one flat surface of each washer is a north magnetic pole while the other flat surface is a south magnetic pole, each of the paired and matching washers being positioned whereby those surfaces of each pair of ferrous washers abutting the skin are of opposing magnetic poles, each of the washers having center holes extending therethrough, the center holes of the inner body portion being associated with the precise location of the corresponding plurality of spots located the skin, the outer body portion magnetically aligning with the inner body portion when brought proximate to the skin.

2. The multiport locator of claim 1 wherein the plurality of openings are circular.

* * * * *

UNITED STATES PATENT AND TRADEMARK OFFICE
CERTIFICATE OF CORRECTION

PATENT NO. : 7,255,682 B1 Page 1 of 1
APPLICATION NO. : 10/936981
DATED : August 24, 2007
INVENTOR(S) : Bartol et al.

It is certified that error appears in the above-identified patent and that said Letters Patent is hereby corrected as shown below:

Title page,

Item (76): The first name of the second inventor should be changed from "Ema" to --Erna--.

Signed and Sealed this

Sixth Day of November, 2007

JON W. DUDAS
*Director of the United States Patent and Trademark Office*